(12) United States Patent
Romanet et al.

(10) Patent No.: US 6,593,477 B1
(45) Date of Patent: Jul. 15, 2003

(54) SYNTHESIS OF 3-ACYLAMINOPYRAZOLES

(75) Inventors: Robert F. Romanet, Rochester, NY (US); Susan M. Fischer, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/282,777

(22) Filed: Oct. 29, 2002

(51) Int. Cl.[7] .............................................. C07D 231/40
(52) U.S. Cl. ................. 548/372.5; 546/275.4; 548/312.4; 548/364.1; 548/371.7
(58) Field of Search ........................... 548/372.5, 364.1; 546/275.4

(56) References Cited

FOREIGN PATENT DOCUMENTS

| JP | 9-278758 | 10/1997 |
|----|----------|---------|
| WO | 01/12189 | 2/2001  |

*Primary Examiner*—Robert W. Ramsuer
(74) *Attorney, Agent, or Firm*—Arthur E. Kluegel

(57) ABSTRACT

Disclosed is a process for forming an N-acylamino pyrazole comprising contacting a N-acyl-3-oxo-imino ether compound either with a salt of hydrazine in the presence of a base or with hydrazine.

17 Claims, No Drawings

SYNTHESIS OF 3-ACYLAMINOPYRAZOLES

FIELD OF THE INVENTION

This invention relates to a process for synthesizing 3-acylaminopyrazole derivatives using hydrazine or a hydrazine salt.

BACKGROUND OF THE INVENTION

3-Acylaminopyrazole derivatives are known in the literature for numerous uses such as in pharmaceutical compositions as possible antitumor agents, enzyme inhibitors, and as useful for treatment of Alzheimer's disease, viral infections, auto-immune diseases and neurodegenerative diseases (see for example WO 01/12189), as bleach stabilizers (see for example DE 2622761), fungicides (see for example JP 62153283), dispersed dyes in photographic applications (see for example JP 07295131), as dye and ink precursors (see for example FR 2167809) and precursors for photographic coupler intermediates (see for example JP 09278758).

There are numerous methods for forming 3-acylaminopyrazoles. The simplest method consists of reacting the 3-aminopyrazole with the appropriate acylating reagent. The problem with this approach is that the acylating agent reacts at the ring nitrogens as well as at the desired exocyclic amino group to yield a mixture of products which leads to lower yields and hard to purify mixtures. This sequence is used in JP 09278758 to acylate 5-amino-3-tert-butyl-1H-pyrazole with pivaloyl chloride in 72.5% yield. Several ways around this problem are described in WO 01/12189 and include 1) oxidizing the amino group of the aminopyrazole to a nitro group, protecting the ring nitrogen with a t-BOC (tert butyloxycarbonate) group, hydrogenating the nitro group back to an amine, acylating with the desired reagent and deblocking the ring nitrogen; and 2) bis-acylating the aminopyrazole on both the desired exocylic nitrogen as well as the ring nitrogen and subsequent hydrolysis of the group on the ring nitrogen. These are long involved sequences which do not proceed in high yield and in the first case involves use of protecting groups which are later discarded wasting material and generating disposal problems and in the second case adding a group only to remove it again likewise wasting materials and causing disposal problems. It is known to react the aminopyrazole directly with an ester to give the desired acylaminopyrazole (J. Heterocyclic Chem. 26, 1713 (1989)) but this sequence involves elevated temperatures and the yield is only 72% crude and 56% purified.

It is a problem to be solved to develop a simple process that provides a high yield synthesis of 3-acylaminopyrazoles.

SUMMARY OF THE INVENTION

The invention provides a process for forming an N-acylamino pyrazole comprising contacting a N-acyl-3-oxo-imino ether compound either with a salt of hydrazine in the presence of a base or with hydrazine. This is a simple process that provides a high yield synthesis of 3-acylaminopyrazoles.

DETAILED DESCRIPTION OF THE INVENTION

The invention is summarized above.

The process of this invention provides pure acylaminopyrazole in high yield. The process, including the two preliminary reactions, is outlined below.

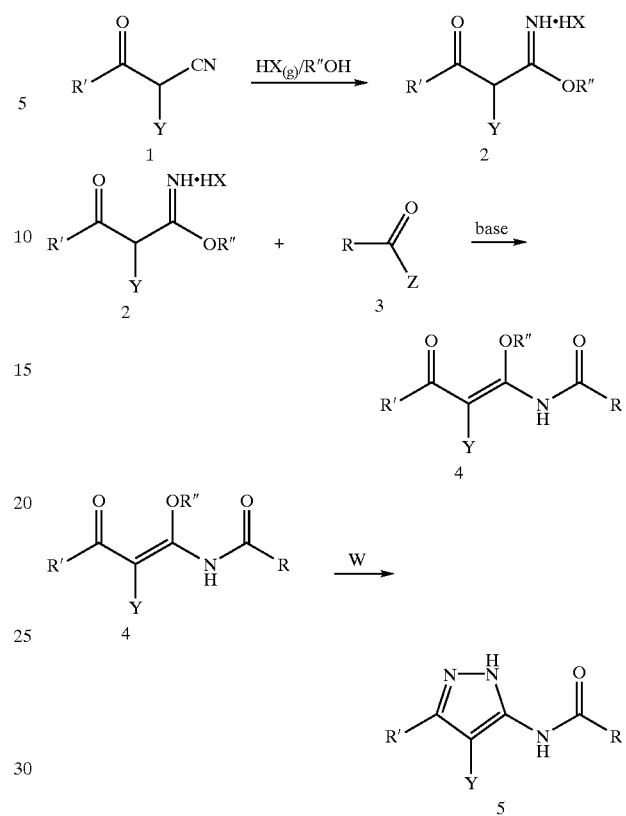

W is hydrazine or a salt of hydrazine provided that, when W is a salt, the reaction is carried out in the presence of a base.

An appropriate β-ketonitrile is subjected to the Pinner reaction to yield the imino ether which after neutralization is reacted with an acylating reagent and then reacted with hydrazine or a salt of hydrazine to give good yields of the 3-acylaminopyrazole. It should be noted that 1 and 2 can exist in tautomeric forms and furthermore that structures 4 and 5 can exist as mixtures of tautomeric forms as shown below.

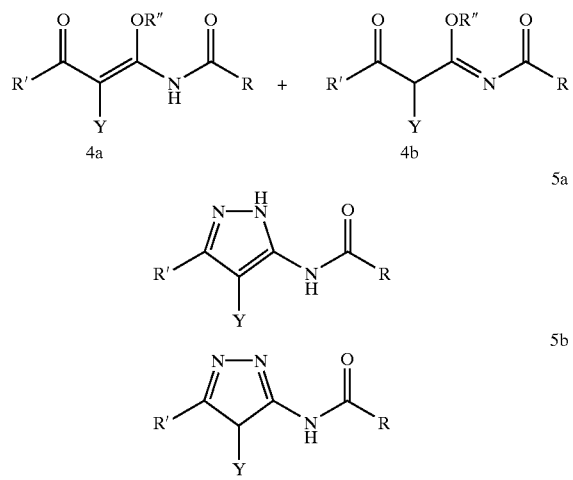

-continued

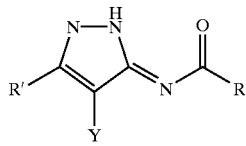

5c

In 4 the tautomeric forms can sometimes be isolated although both forms react to yield the pyrazole. In addition, there are other tautomeric forms that may be present for 4 and 5 involving tautomerization of the amide and location of the double bonds in the pyrazole ring. Accordingly, in the present invention, where only one tautomer is indicated for these compounds, the others are also within the scope of the present invention unless specifically noted otherwise.

The β-ketonitriles, 1 are common starting materials in the art and some are available commercially. They undergo the well known Pinner reaction (for review see Ann. Chim. (Paris) [14] 5, 23–27, pp.24–26) with an alcohol R"OH in the presence of an acid or base catalyst to yield an imino ether 2. Other methods of forming imino ethers are also known and may be used. The next step comprises reacting an acylating agent 3 with the neutralized solution of the imino ether 2 to yield the acylated imino ether 4. This simple process for acylating—acyclic β-keto-imino ethers is novel as the only other method reported in the literature is a low yield photolysis of isoxazoles (Tet Let. 28(47), 5797 (1987)) This product 4 can be isolated and without further purification submitted to the next reaction or without isolation and in the same reaction vessel be treated with hydrazine to yield the acyaminopyrazoles 5. If the reaction product 4 is isolated, no base needs to be used in the subsequent step but if both reactions are run in the same vessel without isolation extra hydrazine must be added or a strong base needs to be added along with the hydrazine. It is fortuitous that in this last reaction the pyrazole is formed exclusively; one might expect to also obtain triazole as well. It will be appreciated that compounds 4 and 5 can exist in tautomeric forms as described in the summary of the invention.

In the formulas 1, 2, 3, 4, 5, R can be an alkyl, aryl, heterocyclic or heteroatom-linked group. R' can be an alkyl, aryl, or heterocyclic group linked to the rest of the compound by a fully substituted carbon atom in R', and R" can be an alkyl, aryl, or heterocyclic group. X is a conjugate base of strong acid e.g. Cl⁻, HSO₄⁻, H₂PO₃⁻, CF₃CO₂ Y is a optionally substituted alkyl or aryl group, H, Cl, Br, OR (R has same meaning as above), the nitrogen of a heterocyclic group such as hydantoin, benzotriazole, imidazole, succinimide, etc. and Z is a Cl, Br, imidazole, OCOR (where R has meaning above) or any such group that renders RCO an acylating group.

Preferably, R is an optionally substituted alkyl, aryl, or heterocyclic group containing no ionizable or nucleophilic substitutents such as OH, or NH₂. Preferably, R' is an optionally substituted alkyl, aryl, or heterocyclic group linked to the rest of the compound by a fully substituted carbon atom and containing no ionizable or nucleophilic substitutents such as OH or NH₂; Desirably, X is a Cl⁻ or HSO₄⁻ radical; Y is a H, Cl, Br, OR (R has same meaning as above); and Z is a Cl, Br, imidazole, or OCOR (where R has meaning above).

More preferably, R is an optionally substituted alkyl, aryl, heterocyclic group containing no ionizable or nucleophilic substitutents such as OH or NH₂; R' is an optionally substituted tertiary alkyl, aryl, heterocyclic group linked to the rest of the compound by a fully substituted carbon atom, containing no ionizable or nucleophilic substitutents such as OH or NH₂; R" is an unsubstituted alky or aryl, group; X is a Cl; Y is a H; and Z is a Cl.

The base in the acylation reaction above can be any inorganic or organic base which doesn't cause decomposition of the starting material such as sodium hydroxide, sodium carbonate, sodium bicarbonate, potassium hydroxide, potassium carbonate, potassium bicarbonate, sodium acetate, potassium acetate, triethylamine, N,N-diisopropylethylamine, N,N-dimethylaniline, pyridine, 2,6-lutidene, N,N-dimethylaminopyridine. Preferably the base is sodium bicarbonate, sodium carbonate, potassium carbonate, potassium bicarbonate, sodium acetate, potassium acetate, pyridine, 2,6-lutidene, N,N-dimethylaniline, More preferably the base is sodium bicarbonate, sodium carbonate, 2,6-lutidene, N,N-dimethylaniline, or pyridine. The amount of base can vary from 2 equivalents to 4 equivalents but is preferably between 2 and 3 equivalents and more preferably 2.2–2.5 equivalents. The solvent for the acylation reaction can be any solvent that will be inert to the acylating reagent such as tetrahydrofuran, dioxane, toluene, ethyl acetate, propyl acetate, diethyl ether, isopropyl ether, N,N-dimethylformamide, N,N-dimethylacetamide, dimethyl sulfoxide, methylene chloride, chloroform, carbon tetrachloride, 1,2-dichloroethane, 1,2-dimethoxyethane, acetonitrile, toluene, hexane, heptane, or cyclohexane. Preferably the solvent for the first reaction is toluene, ethyl acetate, diethyl ether, methylene chloride, acetonitrile, hexane, and more preferably the solvent is ethyl acetate, methylene chloride, or toluene. The temperature of the acylation reaction can be anywhere from −78° C. to 100° C. but preferably between −20° C. and 20° C. and most preferably at 0° C.–5° C. The acylation reaction can be let run until convenient to work up but preferably less than 6 hours and most preferably less than 2 hours. The acylation reaction doesn't need to be run under an inert atmosphere but exclusion of water is desirable.

If the intermediate 4 is not isolated, a particular base or excess hydrazine must be used in the final reaction. Suitable bases in the non-isolation sequence can be any strong organic anhydrous base such as triethylamine, N,N-diisopropylethylamine, DBU (1,8-diazabicyclo[5.4.0] undec-7-ene), 1,1,3,3-tetramethylguanidine, or DABCO (1,4-diazabicyclo[2.2.2]octane), but preferably triethylamine, N,N-diisopropylethylamine, DBU and more preferably triethylamine or N,N-diisopropylethylamine. The amount of base-2 or excess hydrazine is between 2 and 10 equivalents and preferably between 3 and 5 equivalents and more preferably between 3 and 3.5 equivalents. Hydrazine, hydrazine hydrate, or one of its salts such as hydrazine hydrochloride, hydrazine sulfate, hydrazine acetate, hydrazine dihydrochloride can be used in the second reaction. Hydrazine or hydrazine hydrate is preferable and more preferable is hydrazine. If a salt of hydrazine is used, an additional number of equivalents of a strong base such as described for base-2 must be used equal to the number of acids forming the hydrazine salt. The amount of hydrazine used is from 1 to 2 equivalents and preferably from 1 to 1.5 equivalents and more preferably 1.1 to 1.2 equivalents. The temperature of the final reaction can be anywhere from −78° C. to 100° C. but preferably from 0° C.tod 40° C. and most preferably from 20 to 30° C. The final reaction can be let run until convenient to work up but typically less than 6 hours and usually less than 1 hour. The final reaction doesn't need to be run under an inert atmosphere or rigorous exclusion of moisture.

If intermediate 4 is isolated, no particular base needs to be used unless the hydrazine employed is in the form of a salt in which case the particular base as described above for non-isolation must be used and the amount of base is equivalent to the number of acids forming the hydrazine salt. Suitable solvents for the hydrazine reaction are methanol, ethanol, isopropanol, tetrahydrofuran, dioxane, ethyl acetate, propyl acetate, ethyl ether, isopropyl ether, methylene chloride, chloroform, toluene, hexane, heptane, cyclohexane, acetonitrile and preferably methanol, ethanol, isopropanol, tetrahydrofuran, ethyl acetate, methylene chloride, and most preferably methanol, ethanol, and isopropanol.

Following are some examples of acylaminopyrazoles which can be prepared by this process but the invention is by no means restricted to these examples.

M-1
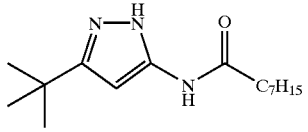

M-2
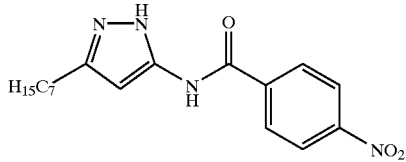

M-3
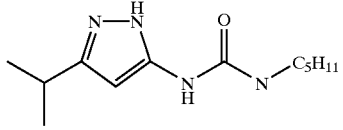

M-4
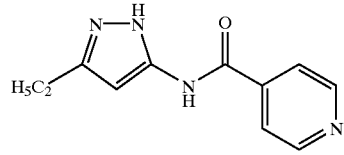

M-5
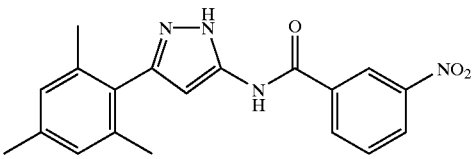

M-6
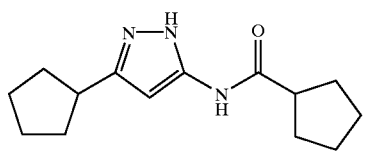

-continued

M-7
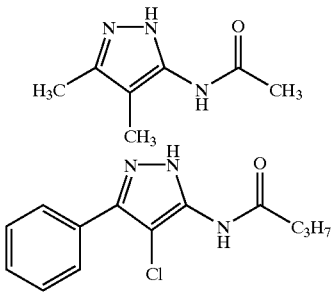

M-8
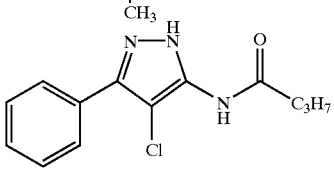

M-9
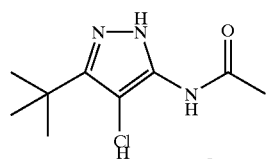

M-10
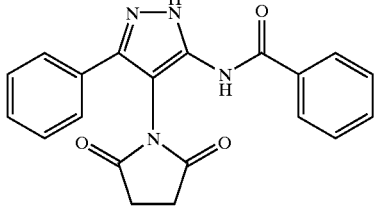

M-11

M-12

M-13

M-14

M-15

M-16

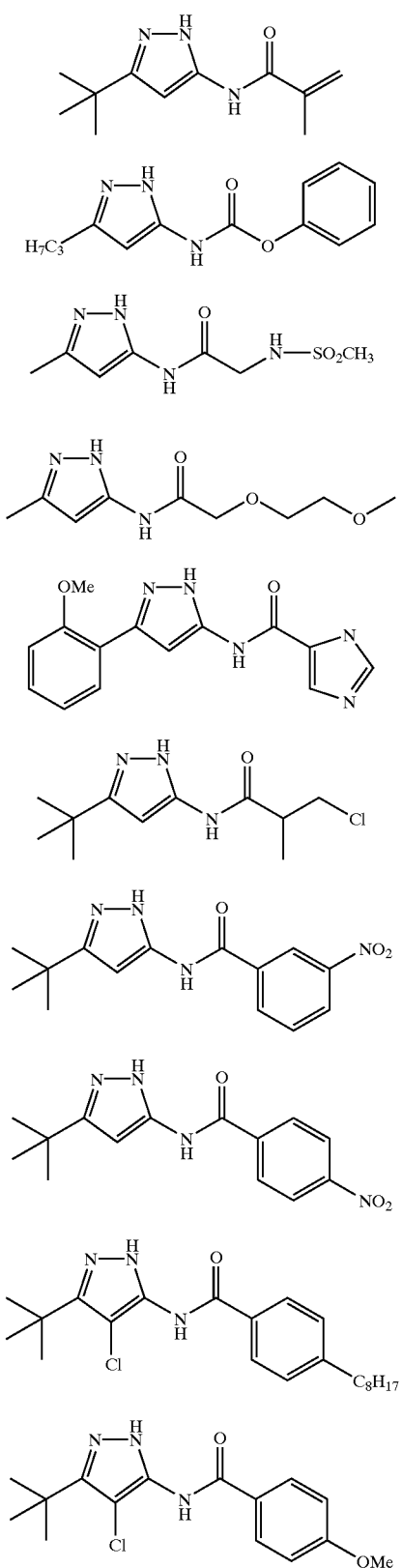

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, The invention provides a simple high yield process for the synthesis of 3-acylaminopyrazoles. Embodiments of the invention require no purification for use in subsequent steps.

phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. If desired, the substituents may themselves be further substituted one or more times with the described substituent groups. When a molecule may have two or more substituents, the substituents may be joined together to form a ring such as a fused ring unless otherwise provided.

The process of the invention can be employed to prepare compounds known as couplers for imaging or for preparing dyes containing pyrazole moieties.

EXAMPLES

Following are the syntheses of several of the compounds of the invention.

Example 1

Synthesis of M-6

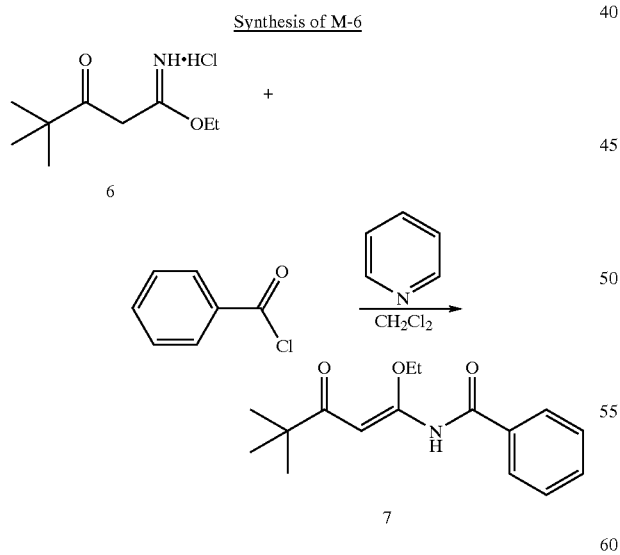

5.0 g (0.0241 mol) of imino ether 6 was added to 4.25 ml (0.0527 mol) pyridine in 25 ml methylene chloride and cooled in an ice bath. The suspension was stirred for 5 minutes and 2.9 ml (0.0250 mol) benzoyl chloride was added dropwise over 3 minutes. The reaction was stirred 5 minutes at ice bath temperatures and the bath removed and the reaction stirred at ambient temperatures one hour. The reaction was poured into 100 ml water and 100 ml ethyl acetate added. After shaking, the aqueous layer was removed, the organic layer washed with water, dried over magnesium sulfate and concentrated to yield 7.0 g (100%) of compound 7 as a clear oil, one spot on TLC. Nmr showed the product to be a mixture of 3 parts of the tautomer shown above and 1 part tautomer where the double bond is between the nitrogen and the carbon bearing the ethoxy group. This material was used in the next step without purification.

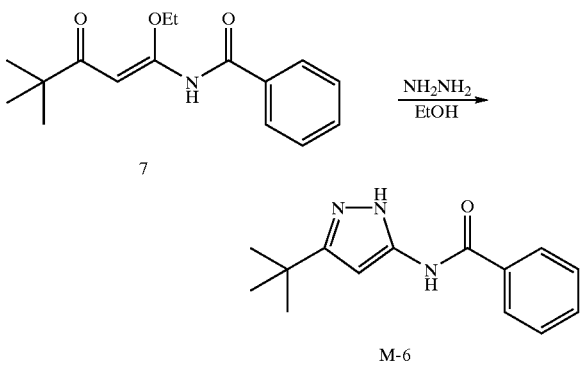

5.0 g (0.0182 mol) compound 7 was dissolved in 50 ml ethanol at room temperature and 0.64 ml (0.0200 mol) hydrazine added dropwise over one minute. After 30 minutes the reaction was poured into water, ethyl acetate added and after shaking, the organic layer was washed once with dilute hydrochloric acid and then with water after which the organic layer was dried over magnesium sulfate and concentrated to 4.1 g (93%) white solid, one spot by TLC and pure by nmr analysis.

Example 2

Synthesis of M-25

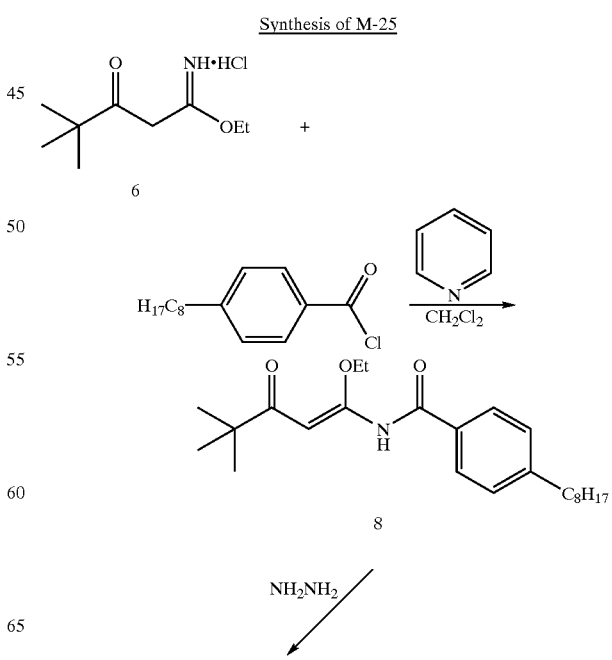

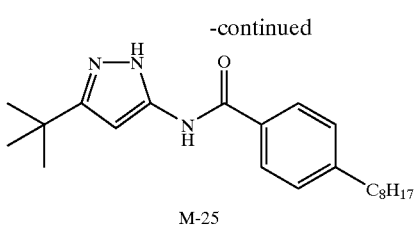

M-25

3.81 ml (0.0473 mol) pyridine and 25 ml of $CH_2Cl_2$ were cooled in an ice bath and 4.5 g (0.0217 mol) of the imino ether 6 were added and stirred 10 minutes. 5.64 g (0.0224 mol) p-octylbenzoylchloride added dropwise over 5 minutes and stirred 4 hours allowing the ice in the bath to melt. The reaction was cooled in an ice bath and 0.720 ml (0.0224 mol) 9.11 ml (0.0652 mol) hydrazine added and the reaction stirred overnight letting the ice melt. The reaction was poured into water, more $CH_2Cl_2$ added and the organic layer separated, washed once with dilute HCl, once with water, dried, and concentrated to 6.8 g solid (89%) pure product.

Example 3

Synthesis of M-23

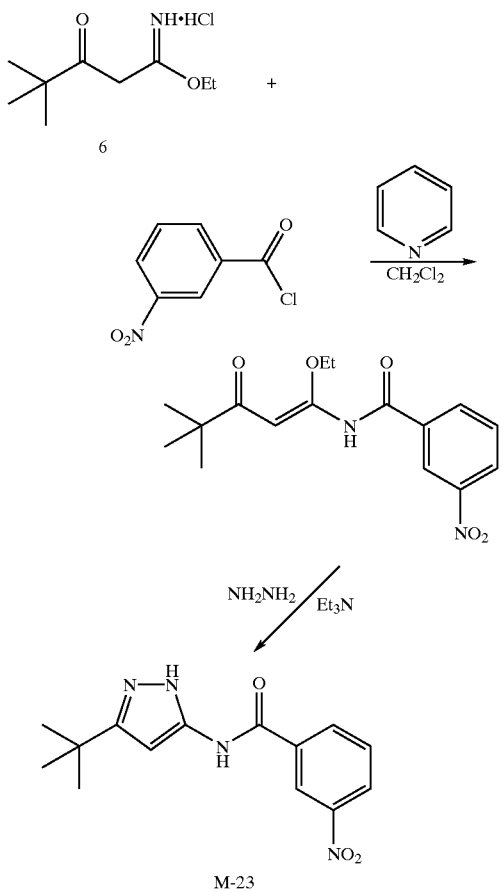

M-23

4.25 ml (0.0527 mol) pyridine and 50 ml of $CH_2Cl_2$ were cooled in an ice bath and 5.0 g (0.0241 mol) of the imino ether 6 were added and stirred 10 minutes. 4.64 g (0.0250 mol) m-nitrobenzoylchloride added portion-wise over 5 minutes and stirred 1 hour allowing the ice to melt. The reaction was cooled in an ice bath and 0.810 ml (0.0253 mol) hydrazine and 10.5 ml (0.0759 mol) added and the reaction stirred 3 hours letting the ice melt. The solvent was evaporated and 100 ml dilute HCl was added and the suspension stirred overnight. The solid was filtered, partially dried on the funnel and stirred 3 hours with 100 ml acetonitrile and collected and dried to yield 6.7 g (97%) white solid, pure by TLC, nmr, and ms.

The invention has been described in detail with particular reference to certain preferred embodiments thereof, but it will be understood that variations and modifications can be effected within the scope of the invention. The entire contents of the patents and other publications referred to in this specification are incorporated herein by reference.

What is claimed is:

1. A process for forming an N-acylamino pyrazole represented by Equation I:

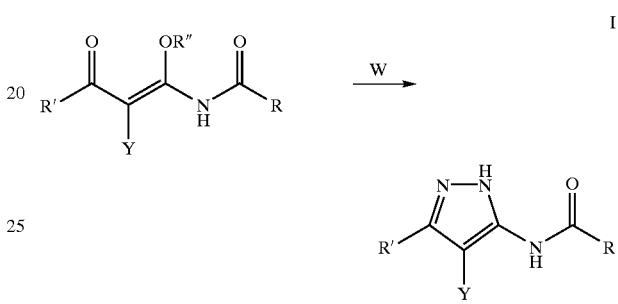

wherein
R is an alkyl, aryl, heterocyclic or hetero atom group;
R' is an alkyl, aryl, or heterocyclic group;
R" is an alkyl, aryl, or heterocyclic group;
Y is H, alkyl, or aryl, or a group linked to the compound by a heteroatom in Y;
W is hydrazine or a salt of hydrazine provided that, when W is a salt, the reaction is carried out in the presence of a base.

2. The process of claim 1 wherein the base is selected from triethylamine, N,N-diisopropylethylamine, DBU (1,8diazabicyclo[5.4.0]undec-7-ene), 1,1,3,3-tetramethylguanidine, and DABCO (1,4-diazabicyclo[2.2.2]octane).

3. The process of claim 1 wherein W is hydrazine.

4. The process of claim 1 wherein W is a salt of hydrazine.

5. The process of claim 1 wherein R' is an alkyl, aryl, or heterocyclic group linked to the rest of the compound by a fully substituted carbon atom in R'.

6. The process of claim 3 wherein R' is a t-butyl, methylcyclopropyl, or adamantyl group.

7. The process of claim 1 wherein R is an alkyl or aryl group.

8. The process of claim 1 wherein R is an alkyl group of at least 8 carbon atoms.

9. The process of claim 1 wherein R is a phenyl group.

10. The process of claim 4 wherein the base is selected from triethylamine or N,N-diisopropylethylamine.

11. The process of claim 1 wherein the reaction temperature is between 0 and 40° C.

12. The process of claim 1 wherein the reaction is carried out in the presence of a solvent comprising methanol, ethanol, isopropanol, tetrahydrofuran, dioxane, ethyl acetate, propyl acetate, ethyl ether, isopropyl ether, methylene chloride, chloroform, toluene, hexane, heptane, cyclohexane, or acetonitrile.

13. The process of claim 1 wherein the reaction I is preceded by reaction II:

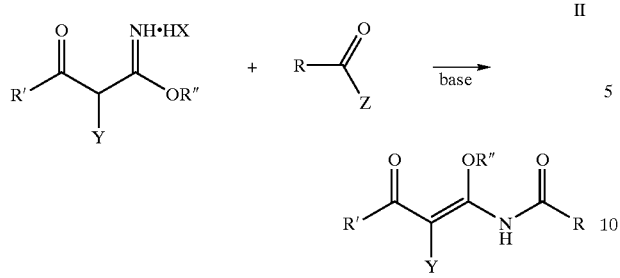

wherein Z is an acylation leaving group.

14. The process of claim 13 wherein Z is selected from Cl, Br, imidazole, and acyloxy.

15. The process of claim 1 wherein the product of reaction II is employed in reaction I without isolation of the product after treatment with a base.

16. The process of claim 15 where the base is selected from triethylamine or N,N-diisopropylethylamine, DBU (1,8-diazabicyclo[5.4.0]undec-7-ene), 1,1,3,3-tetramethylguanidine, or DABCO (1,4-diazabicyclo[2.2.2]octane).

17. The process of claim 13 wherein the reaction II is preceded by reaction III:

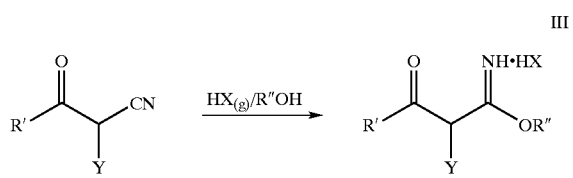

wherein X is the conjugate base of a strong acid.

* * * * *